US00PP26036P3

(12) United States Plant Patent
Byrd

(10) Patent No.: US PP26,036 P3
(45) Date of Patent: Nov. 3, 2015

(54) ***LANTANA CAMARA* PLANT NAMED 'CCCF1'**

(50) Latin Name: *Lantana camara*
Varietal Denomination: CCCF1

(71) Applicant: Douglas B. Byrd, Lucedale, MS (US)

(72) Inventor: Douglas B. Byrd, Lucedale, MS (US)

( * ) Notice: Subject to any disclaimer, the term of this patent is extended or adjusted under 35 U.S.C. 154(b) by 204 days.

(21) Appl. No.: 13/998,489

(22) Filed: Nov. 5, 2013

(65) Prior Publication Data

US 2015/0128319 P1 May 7, 2015

(51) Int. Cl.
*A01H 5/02* (2006.01)

(52) U.S. Cl.
USPC ..... Plt./227

(58) Field of Classification Search
USPC ..... Plt./227
See application file for complete search history.

*Primary Examiner* — Anne Grunberg
(74) *Attorney, Agent, or Firm* — Samuel R. McCoy, Jr.

(57) ABSTRACT

'CCCF1' is a distinctive variety of *Lantana camara* which is characterized by a dwarf, compact growth habit and dark red flowers at anthesis.

3 Drawing Sheets

Latin name of the genus and species: The Latin name of the genus and species of the novel variety disclosed herein is *Lantana camara*.

Variety denomination: The inventive variety of *Lantana camara* disclosed herein has been given the variety denomination 'CCCF1'.

BACKGROUND OF THE INVENTION

The present invention relates to a new and distinct perennial variety of *Lantana camara*, which has been given the variety denomination of 'CCCF1'. Its market class is PLT/227. 'CCCF1' is a woody ornamental whose intended use is for landscaping and as a decorative plant in ornamental containers.

Parentage: The *Lantana camara* variety 'CCCF1' was discovered at a wholesale nursery in Lucedale, Miss., as a spontaneous mutation in a production crop of *Lantana camara* 'Anne Marie' (U.S. Plant Pat. No. 11,310). In April of 2010, while inspecting said crop, one plant in a group of several hundred vegetative cutting progeny of the parent cultivar was observed to have the dwarf, compact habit with dark red flowers at anthesis as opposed to the typical pink flowers of the parent.

Asexual Reproduction: 'CCCF1' was first propagated asexually by vegetative cuttings at a wholesale nursery in Lucedale, Miss. and has since been asexually propagated through three successive generations. The distinctive characteristics of the inventive 'CCCF1' variety are stable from generation to generation; clones of the variety produced by asexual reproduction maintain the distinguishing characteristics of the original plant.

SUMMARY OF THE INVENTION

'CCCF1' is a distinctive variety of *Lantana camara* 'Anne Marie' which is characterized by dwarf, compact growth habit and dark red flowers at anthesis.

BOTANICAL DESCRIPTION OF THE PLANT

Figure 1:
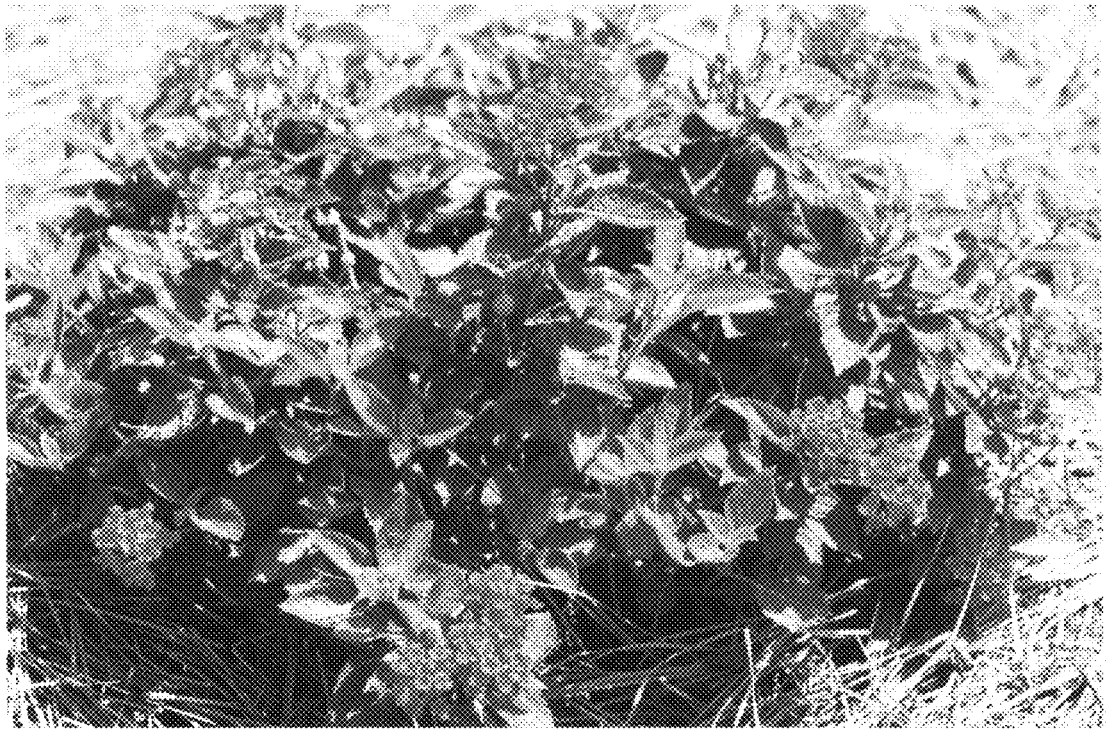
FIG. 1 illustrates an exemplary mature 'CCCF1' plant of approximately one year in age.
Figure 2:
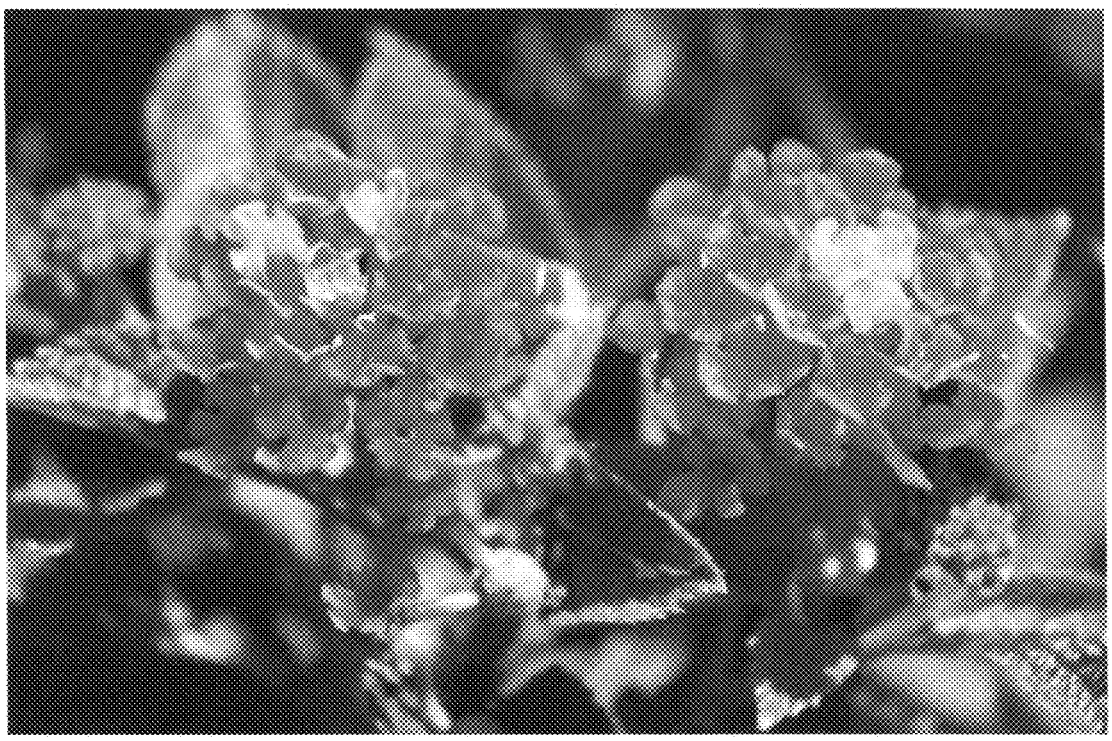
FIG. 2 illustrates the exemplary inflorescence of a 'CCCF1' plant, prior to complete anthesis, with yellow immature flowers near the bud apex and red, near-mature flowers along the peripheral of the inflorescence.
Figure 3:
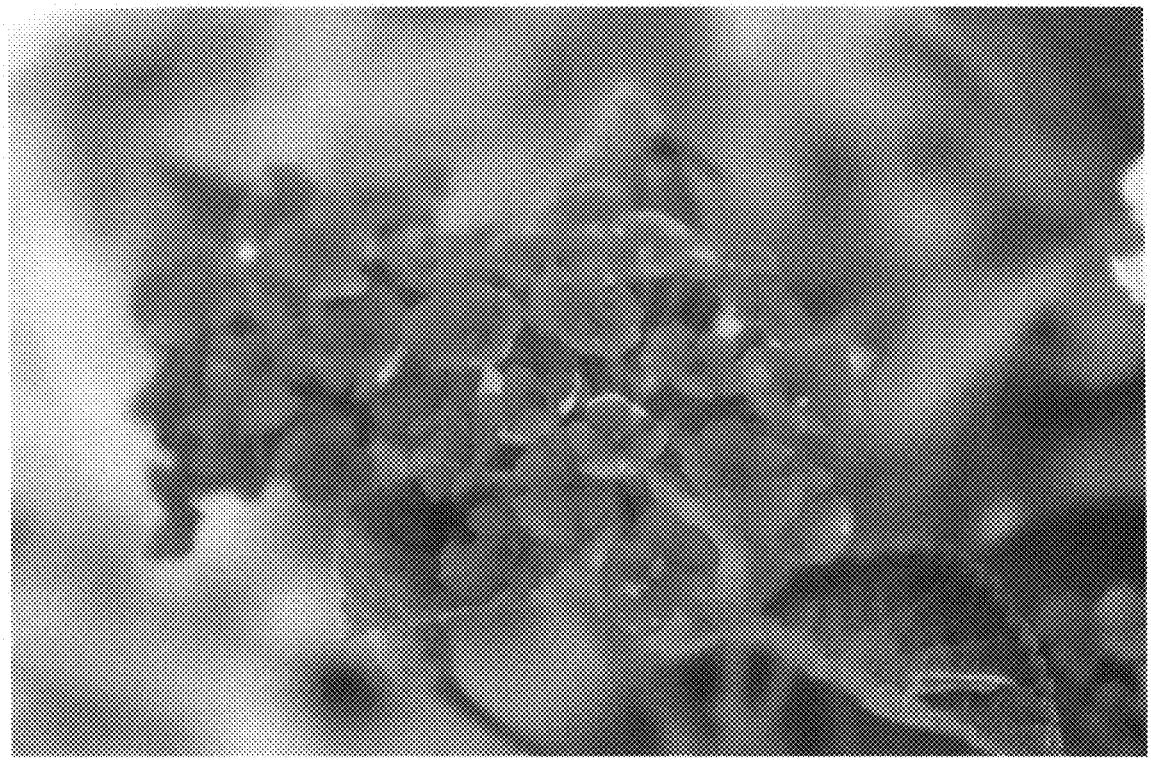
FIG. 3 illustrates the exemplary inflorescence of a 'CCCF1' plant, at complete anthesis.

The following is a detailed botanical description of a new and distinct variety of a *Lantana camara* ornamental plant known as 'CCCF1'. Plant observations were made on plants grown at a wholesale nursery in Lucedale, Miss. Unless indicated otherwise, the descriptions disclosed herein are based upon observations made from 4-month old 'CCCF1' plants grown from rooted cuttings from March 2013 to June 2013 in 15 cm nursery pots filled with soilless potting media, maintained with granular slow release fertilizer and regularly watered with overhead irrigation. No pest and disease measures were taken.

Those skilled in the art will appreciate that certain characteristics will vary with older or, conversely, younger plants. 'CCCF1' has not been observed under all possible environmental conditions. Where dimensions, sizes, colors and other characteristics are given, it is to be understood that such characteristics are approximations or averages set forth as accurately as practicable. The phenotype of the variety may vary with variations in the environment such as season, temperature, light intensity, day length, cultural conditions and the like. Color notations are based on *The Royal Horticultural Society Colour Chart*, The Royal Horticultural Society, London, 1986 edition. Note that generic color descriptions such as 'red' do not exist in the R.H.S. charts and the corresponding R.H.S. colors are quoted.

'CCCF1' is a perennial *Lantana camara* plant which is a spontaneous mutation of *Lantana camara* 'Anne Marie'. After its selection, 'CCCF1' was asexually propagated by division. 'CCCF1' has a dwarf, compact growth habit and dark red flowers. These features and other characteristics are apparent from the description provided below.

Growth Habit, Dimensions and Color

Plant description:

*Plant habit*.—Perennial subshrub; rotund to mounded, compact, and dense.

*Height*.—35 cm at maturity.

*Width*.—35 cm at maturity.

*Growth rate*.—Medium vigor.

*Bloom period*.—Spring to autumn.

*Hardiness*.—USDA Zone 8 to 11.

*Environmental tolerances*.—Drought tolerant once established.

*Pest and disease susceptibility or resistance*.—In common with the species; none of note.

*Propagation*.—Propagation is accomplished using softwood cuttings and plants root well without the use of a rooting compound or hormone. Time to initiate root development is approximately 2 weeks. An average crop time is approximately 2 months to produce a mature and marketable 15-centimeter container, beginning with a rooted cutting.

Roots: Fibrous and freely branched.

Stems & branches:

*Branching and habit*.—Lateral branches, freely branching from multiple primary stems (three observed); two lateral branches arising at each node. Upright and becoming slightly decumbent with age.

*Primary stem dimensions*.—As measured, 160 mm long and 5 mm wide at the base.

*Primary stem internode length*.—Approximately 30 mm.

*Primary stem strength*.—Medium; slightly rigid.

*Primary stem shape*.—Generally square.

*Primary stem color*.—Ranges from yellow-green 144A in immature stems to grey-brown 199A to 199D at maturity.

*Primary stem texture*.—Soft and scrabrous when young and becoming woody with light pubescence with age.

*Lateral branch dimensions*.—Longest branches measured at 90 mm in length with a diameter of 2 mm near the base.

*Lateral branch internode length*.—Ranges from 15 to 45 mm.

*Lateral branch strength*.—Weak to medium rigidity.

*Lateral branch shape*.—Round yet angular.

*Lateral branch color*.—Closest to yellow-green 144A to 144B.

*Lateral branch texture*.—Scabrous and pubescent.

Foliage:

*Type*.—Deciduous.

*Division*.—Simple.

*Arrangement*.—Opposite.

*Attachment*.—Petiolate.

*Shape*.—Ovate.

*Apex*.—Acute.

*Base*.—Obtuse.

*Cross-section*.—Slightly concave.

*Venation*.—Pinnate.

*Vein color* (*adaxial surfaces*).—Midrib is yellow-green 144B; all other veins are indistinguishable from surrounding foliage.

*Vein color* (*abaxial surfaces*).—Yellow-green 144B.

*Margins*.—Serrate.

*Texture*.—Scabrous with both surfaces pubescent.

*Mature leaf dimensions*.—Approximate length 50 mm, average width 35 cm.

*Leaf color* (*adaxial surface*).—Juvenile: yellow-green 144A; mature: green 137A.

*Leaf color* (*abaxial surface*).—Juvenile: yellow-green 144B; mature: green 138A.

*Petiole*.—Length is approximately 14 to 16 mm; width is approximately 1.5 mm. Color is yellow-green 144B. Texture is scabrous and lightly pubescent.

*Stipules*.—None.

Inflorescence:

*Type*.—Terminal and axillary umbels approximately 3 to 4 cm across, borne on upright peduncles, each with approximately 20 to 26 upward-facing, salverform flowers that are sessile to an ovate receptacle; flowers persist for approximately 5 to 7 days; self cleaning. Potentially two inflorescences per node.

*Peduncle*.—At full anthesis, peduncles from 35 to 45 mm long and approximately 1 mm wide; texture is pubescent. Color is yellow-green 144B.

Flowers:

*Bud*.—Shape is oblong; apex is rounded; dimensions are approximately 8 to 10 mm long and 5 mm wide at 2 to 4 days prior to bud-break. Color is yellow-green 145A.

*Calyx*.—Synsepalous; tubular in shape with two acutely pointed sepal lobes. Sepal dimensions are approximately 2 mm long and 1 mm wide. Texture is glabrous. Color is yellow-green 154D.

*Bracts*.—Shape is lanceolate; Apex is acute; Color is yellow-green 145B; texture is pubescent; approximately 4 mm long and 1 mm wide.

*Corolla*.—Salverform flowers with a scalloped outer corolla whose aspect is approximately perpendicular to a relatively long floral tube; over all dimensions are 7 mm across the outer corolla and 12 mm deep, from base of floral tube to the outer corolla. Width of the floral tube is approximately 2 mm.

*Petals*.—Sympetalous with five fused petals; Apex: rounded; Margin: entire to slightly fringed; Texture: glabrous on upper surface of outer corolla and pubescent on lower surface of outer corolla and both the outer and inner surfaces of the floral tube.

*Petal color* (*prior to anthesis*).—Yellow 12A.

*Petal color* (*at anthesis*).—Red 45A to 45B.

Reproductive organs:

*Stamens*.—Four.

*Stamen dimensions*.—About 3 to 4 mm in length and very thin.

*Attachment*.—Adnate to floral tube.

*Anther shape*.—Bilobate.

*Anther length*.—Approximately 1 mm.

*Anther color*.—Black 202A.

*Pistil*.—One.

*Pistil dimensions*.—About 3 mm in length and very thin.

*Stigma*.—Minute and translucent.

*Style color*.—Near translucent with a faint combination of greyed-white 156B and red 42A.

*Ovary position*.—Hypogynous.

*Ovary color*.—Grey-white 156B.

Fruit and seed production:

*Type*.—Drupe.

*Shape*.—Round.

*Diameter*.—Approximately 4 to 5 mm.

*Mature color*.—Black 202A.

*Number per infructescence*.—3 to 5.

Comparison of CCCF1 with Other Varieties of *Lantana camara*

By comparison with the parent, 'CCCF1' has a more compact growth habit, a slightly smaller leaf size and mature flowers that are dark red as opposed to fuchsia. Mature flowers of 'CCCF1' are a dark red, corresponding to 45A to 45B, whereas the mature flowers of the parent are generally pink, corresponding to red-purple 67C to 67A. The mature plant dimensions of 'CCCF1' are 35 cm tall by 35 cm wide, whereas the observed height of mature 'Anne Marie' plants is observed at 45 to 60 cm tall and 60 to 75 cm wide. Mature leaves of 'CCCF1' are 50 mm long by 35 mm wide, whereas the leaves of 'Anne Marie' are 57 mm long and 42 mm wide.

'CCCF1' is more comparable in size to *Lantana camara* 'Lucky Lantern Red' (unpatented) and while both varieties are said to have a red mature flower, the flowers of 'Lucky Lantern Red' contain more orange color pigments translating into a flower color of red 42C to orange-red 35A, whereas the flower color of 'CCCF1' is more of a dark red, corresponding to 45A to 45B.

The combination of its dense growth habit and dark red flowers makes 'CCCF1' a desirable ornamental plant suited for mass production for pot and landscape use.

That which is claimed is:

1. A new and distinct variety of *Lantana camara* plant named 'CCCF1', substantially as described and illustrated herein.

* * * * *